__United States Patent__ [19]

Yamatsu et al.

[11] 4,346,109

[45] Aug. 24, 1982

[54] METHOD OF TREATING KERATOTIC SKIN DISEASE

[75] Inventors: Isao Yamatsu, Kawaguchi; Yuichi Inai, Tokyo; Shinya Abe, Kawagoe; Takeshi Suzuki, Abiko; Yoshikazu Suzuki, Ichinomiya; Osamu Tagaya, Gifu; Nozomu Koyanagi, Niiza, all of Japan

[73] Assignee: Eisai Co., Ltd., Tokyo, Japan

[21] Appl. No.: 249,290

[22] Filed: Mar. 30, 1981

[30] Foreign Application Priority Data

Jul. 31, 1980 [JP] Japan .................................. 55-104420

[51] Int. Cl.$^3$ .............................................. A61K 31/20
[52] U.S. Cl. .................................... 424/318; 424/344
[58] Field of Search ................................. 424/318, 344

[56] References Cited

U.S. PATENT DOCUMENTS

| | | | |
|---|---|---|---|
| 3,934,028 | 1/1976 | Lee ...................................... | 424/318 |
| 3,966,967 | 6/1976 | Lee ...................................... | 424/318 |
| 4,107,193 | 8/1978 | Kijiima et al. ...................... | 260/410 |
| 4,147,708 | 4/1979 | Manchand .......................... | 260/413 |

Primary Examiner—Leonard Schenkman
Attorney, Agent, or Firm—Blanchard, Flynn, Thiel, Boutell & Tanis

[57] ABSTRACT

A compound, 3,7,11,15-tetramethyl-2,4,6,10,14-hexadecapentaenoic acid, and a salt thereof are disclosed as a therapeutic agent for treatment of skin diseases with keratinization.

6 Claims, No Drawings

METHOD OF TREATING KERATOTIC SKIN DISEASE

This invention relates to a compound of 3,7,11,15-tetramethyl-2,4,6,10,14-hexadecapentaenoic acid having the formula (I):

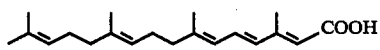 (I)

and a salt thereof and a therapeutic agent for treatment of skin diseases with keratinization which contains the same.

Examples of the salts of the compound of the general formula (I) include its sodium salt and its potassium salt.

The compound of the aforementioned formula (I) provided by the present invention shows therapeutic activity for treatment of skin diseases with keratinization.

Examples of the skin diseases with keratinization which can be treated by the compound of the formula (I) include skin diseases showing symptoms such as hyperkeratosis, parakeratosis and dyskeratosis. More concretely, examples of the skin diseases include psoriasis, acne, acne vulgaris, Darier's disease, palmoplantar pustulosis, lichen planus, ichthyosis, erythroderma, pityriasis rubra pilasis, and keratosis senilis.

There are employed steroid-type external preparations for the treatment of the skin diseases with keratinization. These preparations, however, have strong side-effects, so that they are not suitable for repeated administration for a long period and treatment with administration of a great amount of the preparation.

In contrast, 3,7,11,15-tetramethyl-2,4,6,10,14-hexadecapentaenoic acid of the present invention has activity for inhibition of keratinization of skin and shows low toxicity.

The results of pharmacological tests and toxicity tests conducted on the compound of the present invention are set forth below.

Pharmacological Tests (Inhibition of Keratinization)

(1) Experimental procedure

The procedure is disclosed by Kawamura, in "Gann" 70, 483 (1979), using rat bladder.

Into a Petri dish (diameter 6 cm) in which 8 coverglasses (diameter 15 mm) were placed was poured 5 ml. of a suspension of variant epithelial cells of rat bladder named BES 20B (approximately $2 \times 10^5$ cells/ml.), and the incubation was carried out at 37° C., for 24 hours and at 5% carbon dioxide concentration. Each of the so treated coverglasses was placed in 2 ml. of Eagle's MEM medium containing the test compound at different concentrations, and then another incubation was carried out at 37° C. and at 5% carbon dioxide concentration. The medium was renewed at intervals of 2-3 days. On the 2nd, 5th, 8th and 14th days from the beginning of the incubation, the cover glass was taken out of the medium and subjected to Papanicolaou stain treatment to observe the degree of keratinization. The observation was carried out by the measurement of the absorption spectrum in the region of 400–750 nm, and the KI (Keratinization Index) was calculated from the following equation.

$$KI = \frac{\text{Absorption peak in the vicinity of 490 nm ascribed to the keratinized cells}}{\text{Absorption peak in the vicinity of 640 nm ascribed to the non-keratinized cells}}$$

A value of the KI of 1.0 or higher indicates high keratinization, and a value of the KI of 0.5 or less indicates substantially no keratinization.

The BES 20B cells were also incubated in a medium containing no compound of the invention, for comparison.

(2) Test compound 3,7,11,15-Tetramethyl-2,4,6,10,14-hexadecapentaenoic acid (the compound according to the present invention).

(3) Experimental results

The results are set forth in Table 1.

TABLE 1

| | KI Period of Incubation | | | |
|---|---|---|---|---|
| | 2 days | 5 days | 8 days | 14 days |
| Control | 0.43 | 1.10 | 3.27 | 3.08 |
| Compound of the Invention | | | | |
| 0.1 μg./ml. | 0.43 | 0.67 | 0.55 | 0.52 |
| 1.0 μg./ml. | 0.42 | 0.46 | 0.38 | 0.39 |
| 5.0 μg./ml. | 0.48 | 0.50 | — | 0.22 |

In the experiment on the control, the KI value exceeded 1.0 on the 5th day from the beginning of incubation, which indicates high keratinization. In contrast to the result on the control, the results given by different concentrations of the compound of the present invention showed the KI values of less than 1.0 for all runs to indicate inhibition of keratinization.

Toxicity Tests (1) Experimental procedure

The test compound was administered repeatedly to a group of 6 mice (ICR strain, female) for 14 days. The amount of the administration was 40 mg./Kg./day, 200 mg./Kg./day, and 400 mg./Kg./day for the compound of the present invention. In the course of the administration, increase or decrease of the weight of the mouse, occurrence of death, etc. were observed.

(2) Test compound

The compound described in the pharmacological tests was employed.

(3) Experimental results (a) Increase and decrease of the weight
The results are set forth in Table 2.

(b) Death
No deaths were observed on the mice treated with the compound of the present invention.

(c) Falling-out of hair
No falling-out of hair was observed on the mice treated with the compound of the present invention.

(d) Cyanosis
No cyanosis was observed on mice treated with the compound of the present invention.

TABLE 2

| Test Compound | Amount of Administration (mg./Kg./day) | Average of Weight (g) | | | | | | |
|---|---|---|---|---|---|---|---|---|
| | | 0 | 2 | 4 | 6 | 8 | 10 | 12 | 14 |
| No administration | | 20.5 | 22.3 | 22.1 | 22.1 | 22.0 | 22.3 | 23.0 | 23.6 |
| Compound (I) of the Invention | 40 | 20.9 | 22.4 | 22.2 | 22.6 | 23.1 | 23.0 | 22.6 | 24.0 |
| | 200 | 21.4 | 21.7 | 20.0 | 21.9 | 22.8 | 22.9 | 23.3 | 24.1 |
| | 400 | 25.4 | 26.5 | 28.0 | 26.4 | 26.3 | 26.6 | 26.3 | 27.0 |

Among the subjects of the toxicity tests, the falling-out of hair and the weight change are known to indicate hypervitaminosis of Vitamin A. No such problem was observed on the group of mice treated with the compound of the present invention.

In view of the pharmacological test results and the toxicity test results hereinbefore described, the compound of the present invention is considered to be of high safety and to be of value as a therapeutic agent for treatment of skin diseases with keratinization.

Therefore, the compound of the present invention can be employed for the treatment of skin diseases with keratinization such as acne and psoriasis vulgaris and the treatment of allergic and inflammatory skin diseases. Moreover, the compound of the present invention can be employed for the treatment of mucosal diseases caused by inflammation, degeneration and displastic change.

For applications as a therapeutic agent for treatment of skin disease with keratinization, the compound of the present invention is administered orally in the form of a powder, granules, pellets, hard capsules, etc., or in the form of ointment, suppository, injection solution, etc. The dosage is generally 40 mg.—4 g./day for adult. If the compound of the present invention is employed in the form of an external preparation, the dosage can be varied depending on the conditions of the disease. The compound of the present invention can be combined with a generally employable carrier for medical use in the conventional manner to give the preparations described above.

The processes for the preparation of the compound of the present invention are illustrated by the following examples, but these examples are not intended to restrict the present invention.

EXAMPLE 1

To a suspension of 5.0 g. of 55% sodium hydride (oily) in 60 ml. of n-hexane was added 28.6 g. of triethyl phosphonoacetate. The mixture was then heated under reflux, and 20 g. of 6,10,14-trimethyl-3,5,9,13-pentadecatetraen-2-on was added dropwise to the mixture under stirring. After 30 minutes, the reaction liquid was poured into 200 ml. of water, and then 500 ml. of n-hexane was added for extraction. The n-hexane phase was separated, washed with two 100 ml. portions of a mixture of methanol and water (2:1), and concentrated. The so obtained concentrate was purified by silica gel column chromatography to give 18 g. of ethyl 3,7,11,15-tetramethyl-2,4,6,10,14-hexadecapentaenoate.

To 10 g. of the ethyl 3,7,11,15-tetramethyl-2,4,6,10,14-hexadecapentaenoate obtained above was added a solution of 3.9 g. of potassium hydroxide in 30 ml. of isopropyl alcohol, and the mixture was stirred at 50° C. for 1 hour. The reaction liquid was then poured into ice-water, made acidic by addition of hydrochloric acid, and extracted with 100 ml. of ethyl ether. The ether phase was washed with water, dried over magnesium sulfate, and concentrated to give 9.0 g. of an oil. The oil was dissolved in 50 ml. of n-hexane and crystalized at −20° C. to give 4.0 g. of 3,7,11,15-tetramethyl-2,4,6,10,14-hexadecapentaenoic acid in the form of pale yellow needles.

M.p.: 78.4° C.

Mass spectrum (m/e): 302 (M+)

Infrared absorption spectrum (cm$^{-1}$, KBr tablet): 3450, 2900, 1680, 1595

NMR spectrum (δ, CDCl$_3$): 1.61 (6H, s), 1.68 (3H, s), 1.86 (3H, s), 1.92–2.24 (8H, b), 2.35 (3H, s), 5.10 (2H, b), 5.76 (1H, bs), 5.98 (1H, d, J=11 Hz), 6.20 (1H, d, J=15 Hz), 6.90 (1H, dd, J=11 Hz, 15 Hz), 11.63 (1H, b)

Ultraviolet absorption spectrum: $\lambda_{max.}^{methanol}$ 304 nm

EXAMPLE 2

| Pellet | |
|---|---|
| 3,7,11,15-Tetramethyl-2,4,6,10,14-hexadecapentaenoic acid | 50 g. |
| Silicic acid anhydride | 30 g. |
| Crystalline cellulose | 50 g. |
| Corn starch | 36 g. |
| Hydroxypropylcellulose | 10 g. |
| Magnesium stearate | 4 g. |

The above composition was processed in the conventional manner to give a pellet (180 mg. for a pellet).

What is claimed is:

1. A method for the treatment of skin disease with keratinization, which comprises administering to a subject requiring such treatment a therapeutically effective amount of 3,7,11,15-tetramethyl-2,4,6,10,14-hexadecapentaenoic acid of the formula:

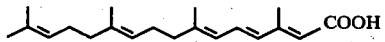

or a pharmaceutically acceptable salt thereof.

2. A method according to claim 1, wherein a dosage of from 40 mg to 4 g per day of said 3,7,11,15-tetramethyl-2,4,6,10,14-hexadecapentaenoic acid or pharmaceutically acceptable salt thereof is administered to an adult patient.

3. A method according to claim 1, wherein said 3,7,11,15-tetramethyl-2,4,6,10,14-hexadecapentaenoic acid or salt thereof is administered orally.

4. A method according to claim 1, wherein said 3,7,11,15-tetramethyl-2,4,6,10,14-hexadecapentaenoic acid or salt thereof is administered by injection.

5. A method according to claim 1, wherein said 3,7,11,15-tetramethyl-2,4,6,10,14-hexadecapentaenoic acid or salt thereof is administered topically.

6. A method according to claim 1, wherein said 3,7,11,15-tetramethyl-2,4,6,10,14-hexadecapentaenoic acid or salt thereof is administered by a suppository.

* * * * *